US009844477B2

(12) United States Patent
Schneider et al.

(10) Patent No.: US 9,844,477 B2
(45) Date of Patent: Dec. 19, 2017

(54) ABSORBENT ARTICLES AND METHOD FOR MANUFACTURING THE SAME

(71) Applicant: The Procter & Gamble Company, Cincinnati, OH (US)

(72) Inventors: Uwe Schneider, Cincinnati, OH (US); Thomas Henrich, Montgomery, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 662 days.

(21) Appl. No.: 14/303,632

(22) Filed: Jun. 13, 2014

(65) Prior Publication Data
US 2014/0290838 A1    Oct. 2, 2014

Related U.S. Application Data

(62) Division of application No. 12/624,851, filed on Nov. 24, 2009, now Pat. No. 8,777,913.

(51) Int. Cl.
*A61F 13/15*    (2006.01)
*B32B 38/04*    (2006.01)
(Continued)

(52) U.S. Cl.
CPC ...... *A61F 13/551* (2013.01); *A61F 13/15723* (2013.01); *A61F 13/15747* (2013.01);
(Continued)

(58) Field of Classification Search
CPC .......... B61F 13/15723; B61F 13/15747; A61F 2013/15715; B32B 38/0004;
(Continued)

(56) References Cited

U.S. PATENT DOCUMENTS 3,860,003 A    1/1975  Buell
4,122,552 A    10/1978 Tedford
(Continued)

FOREIGN PATENT DOCUMENTS

GB    2 303 045 A    2/1997
WO    WO 95/16746 A1   6/1995

OTHER PUBLICATIONS

PCT International Search Report, dated Mar. 31, 2011, 13 pages.

*Primary Examiner* — Linda L Gray
(74) *Attorney, Agent, or Firm* — Charles R. Matson

(57) ABSTRACT

The present disclosure generally relates to absorbent products and methods for manufacturing the same. An absorbent product comprises a backsheet having a first lateral end edge, a second lateral end edge, a first longitudinal side edge, and a second longitudinal side edge. The absorbent product further comprises a first longitudinal line of weakness laterally inboard of the first longitudinal side edge, a second longitudinal line of weakness laterally inboard of the second longitudinal side edge, a first lateral line of weakness longitudinally inboard of the first lateral end edge, and a second lateral line of weakness longitudinally inboard of the second lateral end edge. The absorbent product also comprises a topsheet connected with the backsheet, an absorbent article, the absorbent article having an outer perimeter defined by the first and second longitudinal lines of weakness and the first and second lateral lines of weakness, and a removable trim region.

10 Claims, 12 Drawing Sheets

(51) Int. Cl.
*A61F 13/551* (2006.01)
*B32B 38/00* (2006.01)
*B32B 38/10* (2006.01)

(52) U.S. Cl.
CPC . *A61F 2013/15715* (2013.01); *B32B 38/0004* (2013.01); *B32B 38/10* (2013.01); *Y10T 156/1051* (2015.01); *Y10T 156/1052* (2015.01); *Y10T 156/1056* (2015.01); *Y10T 156/1062* (2015.01); *Y10T 156/1093* (2015.01)

(58) Field of Classification Search
CPC ............ B32B 38/105; Y10T 156/1036; Y10T 156/1052; Y10T 156/1057; Y10T 156/1095; Y10T 156/1097
See application file for complete search history.

(56) References Cited

U.S. PATENT DOCUMENTS

| | | |
|---|---|---|
| 4,326,528 A | 4/1982 | Ryan et al. |
| 4,564,108 A | 1/1986 | Widlund et al. |
| 4,610,678 A | 9/1986 | Weisman et al. |
| 4,630,320 A | 12/1986 | Van Gompel |
| 4,834,735 A | 5/1989 | Alemany et al. |
| 4,888,231 A | 12/1989 | Angstadt |
| 4,917,675 A | 4/1990 | Taylor et al. |
| 5,037,416 A | 8/1991 | Allen et al. |
| 5,087,253 A | 2/1992 | Cooper |
| 5,151,092 A | 9/1992 | Buell et al. |
| 5,260,345 A | 11/1993 | DesMarais et al. |
| 5,269,775 A | 12/1993 | Freeland et al. |
| 5,358,499 A | 10/1994 | Seidy |
| 5,387,207 A | 2/1995 | Dyer et al. |
| 5,397,316 A | 3/1995 | LaVon et al. |
| 5,478,336 A | 12/1995 | Pigneul |
| 5,554,145 A | 9/1996 | Roe et al. |
| H1602 H | 10/1996 | Brock |
| 5,569,234 A | 10/1996 | Buell et al. |
| H1606 H | 11/1996 | Gelnovatch et al. |
| 5,571,096 A | 11/1996 | Dobrin et al. |
| 5,704,929 A | 1/1998 | Bien |
| 5,769,837 A | 6/1998 | Parr |
| 5,989,236 A | 11/1999 | Roe et al. |
| 5,993,430 A | 11/1999 | Gossens et al. |
| 6,004,306 A | 12/1999 | Robles et al. |
| 6,156,424 A | 12/2000 | Taylor |
| 6,524,290 B2 | 2/2003 | Motta et al. |
| 6,994,696 B2 | 2/2006 | Suga |
| 7,427,277 B2 | 9/2008 | Woltman et al. |
| 7,641,641 B2 | 1/2010 | Ramshak |
| 8,105,302 B2 | 1/2012 | Rubio |
| 8,632,518 B2 | 1/2014 | Lavon et al. |
| 2002/0032427 A1 | 3/2002 | Schmitz et al. |
| 2005/0131371 A1 | 6/2005 | Fell et al. |
| 2005/0173292 A1 | 8/2005 | Klose et al. |
| 2005/0177127 A1 | 8/2005 | Ashton et al. |
| 2006/0241558 A1 | 10/2006 | Ramshak |
| 2006/0282057 A1 | 12/2006 | Otsubo et al. |
| 2008/0107861 A1 | 5/2008 | Dalal et al. |
| 2008/0200889 A1 | 8/2008 | Sanders |

ABSORBENT ARTICLES AND METHOD FOR MANUFACTURING THE SAME

CROSS REFERENCE TO RELATED APPLICATION

This application is a divisional of U.S. application Ser. No. 12/624,851, filed Nov. 24, 2009, which is incorporated herein by reference.

FIELD OF THE INVENTION

The present disclosure generally relates to absorbent articles and methods for manufacturing the same, and more particularly relates to absorbent products comprising absorbent articles packaged for individual sale and methods for manufacturing the same.

BACKGROUND OF THE INVENTION

Absorbent articles, such as diapers, for example, can be sold individually. At times, these absorbent articles are sold individually in lower income countries or in areas where consumers cannot afford to purchase an entire package of absorbent articles at a given time. In such an instance, a retailer may open the package of the absorbent articles and then sell individual absorbent articles to consumers at a lower cost than the entire package of the absorbent articles.

SUMMARY OF THE INVENTION

In one non-limiting embodiment, an absorbent product comprises a backsheet having a first lateral end edge, a second lateral end edge, a first longitudinal side edge, and a second longitudinal side edge. The absorbent product further comprises a first longitudinal line of weakness laterally inboard of the first longitudinal side edge, a second longitudinal line of weakness laterally inboard of the second longitudinal side edge, a first lateral line of weakness longitudinally inboard of the first lateral end edge, and a second lateral line of weakness longitudinally inboard of the second lateral end edge. The absorbent product further comprises a topsheet connected with the backsheet, and an absorbent article comprising an absorbent core disposed between the backsheet and the topsheet. The absorbent article has an outer perimeter defined by the first and second longitudinal lines of weakness and the first and second lateral lines of weakness and a removable trim region defined by an area of the backsheet between the outer perimeter of the absorbent article and the first and second longitudinal side edges and the first and second lateral end edges. The backsheet is folded along a lateral axis such that the first lateral end edge is connected with the second lateral end edge, a first portion of the first longitudinal side edge is connected with a second portion of the first longitudinal side edge, and a first portion of the second longitudinal side edge is connected with a second portion of the second longitudinal side edge.

In another non-limiting embodiment, a method for manufacturing an absorbent product comprises the steps of advancing a continuous substrate through a converting line and combining the substrate with a topsheet and an absorbent core. The absorbent core is disposed between the topsheet and the substrate. The method further comprises cutting the substrate to form a backsheet having a first lateral end edge, a second lateral end edge, a first longitudinal side edge, and a second longitudinal side edge. The method further comprises folding the backsheet along a lateral axis and connecting the first lateral end edge with the second lateral end edge, connecting a first portion of the first longitudinal side edge with a second portion of the first longitudinal side edge, and connecting a first portion of the second longitudinal side edge with a second portion of the second longitudinal side edge. The method further comprises creating a first longitudinal line of weakness laterally inboard of the first longitudinal end edge, creating a second longitudinal line of weakness laterally inboard of the second longitudinal end edge, creating a first lateral line of weakness longitudinally inboard of the first lateral end edge, and creating a second lateral line of weakness longitudinally inboard of the second lateral end edge. The lines of weakness define an outer perimeter of an absorbent article comprising the absorbent core disposed between the backsheet and the topsheet. A removable trim region is defined by an area of the backsheet between the outer perimeter of the absorbent article, the first and second longitudinal side edges, and the first and second lateral end edges.

DETAILED DESCRIPTION OF THE INVENTION

Figure 1:
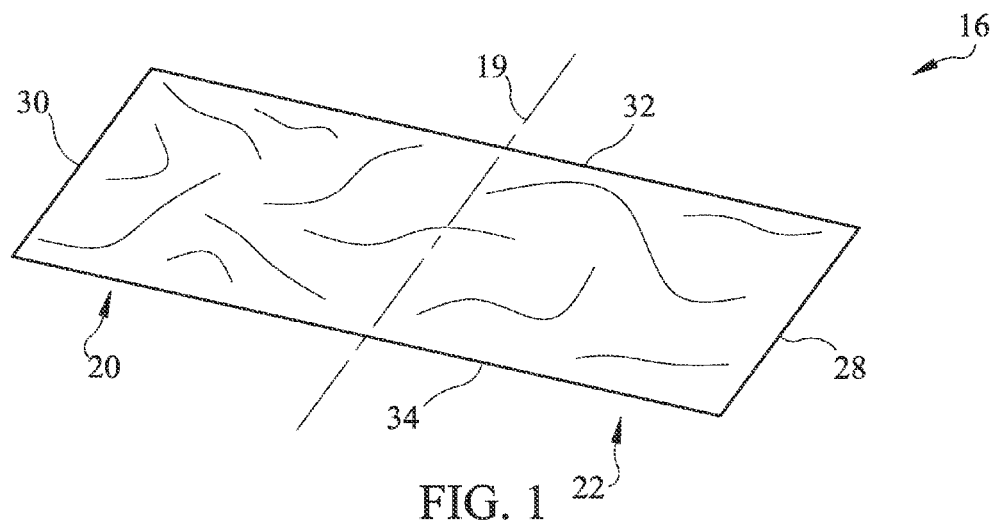
FIG. 1 is a perspective view of a backsheet used in making an absorbent product according to one non-limiting embodiment.

Various non-limiting embodiments of the present disclosure will now be described to provide an overall understanding of the principles of the structure, function, manufacture, and use of the apparatuses and methods disclosed herein. One or more examples of these non-limiting embodiments are illustrated in the accompanying drawings. It is to be appreciated that the apparatuses and methods specifically described herein and illustrated in the accompanying drawings are non-limiting example embodiments and that the scope of the various non-limiting embodiments of the present disclosure are defined solely by the claims. The features illustrated or described in connection with one non-limiting embodiment may be combined with the features of other non-limiting embodiments. It is also to be appreciated that such features can be combined with features of the absorbent articles and methods of manufacture disclosed in the U.S. patent application entitled "ABSORBENT ARTICLES AND METHODS FOR MANUFACTURING SAME," filed Nov. 24, 2009, and identified as Ser. No. 12/624,822. Such modifications and variations are intended to be included within the scope of the present disclosure.

Absorbent articles, such as diapers, training diapers, pull-up pants, incontinence briefs, and undergarments, for example, may be sold individually in various areas or countries, such as in lower income countries or areas, for example. When selling the absorbent articles individually, a retailer opens a package of the absorbent articles, which are not packaged individually. To protect the individual absorbent articles from contaminants, bacteria, and/or dirt forming thereon, after the package is opened, individual absorbent products that maintain wearer facing surfaces of the individual absorbent articles in a sanitary condition prior to use can be provided. In one embodiment, the individual absorbent products can be sealed about at least a portion of an outer perimeter, for example, to maintain the wearer facing surfaces of the individual absorbent articles in a sanitary condition prior to use.

In various embodiments of the present disclosure, referring to FIGS. 1-5, an absorbent product 10, which can be individually sealed, can comprise a chassis 12, which may comprise a main body of the absorbent product 10. The chassis 12 can also comprise an outer covering including a liquid pervious topsheet 14 and/or a liquid impervious backsheet 16. The topsheet 14 can comprise a wearer facing surface 15 and the backsheet 16 can comprise a garment facing surface 17. The chassis 12 can comprise an absorbent core 18 positioned intermediate the topsheet 14 and the backsheet 16. Stated another way, the absorbent core 18 can be sandwiched intermediate the topsheet 14 and the backsheet 16 (see e.g., FIG. 2). In one embodiment, the chassis 12 can be folded about a lateral axis 19 such that a first portion 20 of the chassis 12 can be positioned adjacent to, or substantially adjacent to, (i.e., folded over) a second portion 22 of the chassis 12. In such an embodiment, the first and second portions 20 and 22 can form a first waist region 24 comprising laterally opposing ends 25, a second waist region 27 comprising laterally opposing ends 29, and a crotch region 26 longitudinally intermediate of the first and second waist regions 24 and 27. In one embodiment, the first and second waist regions 24 and 27 may comprise elastic elements such that they gather about a waist of a wearer to provide improved fit and containment of urine and other body exudates, for example. The crotch region 26 is the portion of the absorbent product 10 which is generally positioned between the wearer's legs.

While the topsheet 14, the backsheet 16, and the absorbent core 18 may be assembled in a variety of configurations, some configurations are described generally in U.S. Pat. No. 5,554,145, entitled "Absorbent Article With Multiple Zone Structural Elastic-Like Film Web Extensible Waist Feature", issued to Roe et al. on Sep. 10, 1996; U.S. Pat. No. 5,569,234, entitled "Disposable Pull-On Pant", issued to Buell et al. on Oct. 29, 1996; and U.S. Pat. No. 6,004,306, entitled "Absorbent Article With Multi-Directional Extensible Side Panels", issued to Robles et al. on Dec. 21, 1999.

Figure 2:
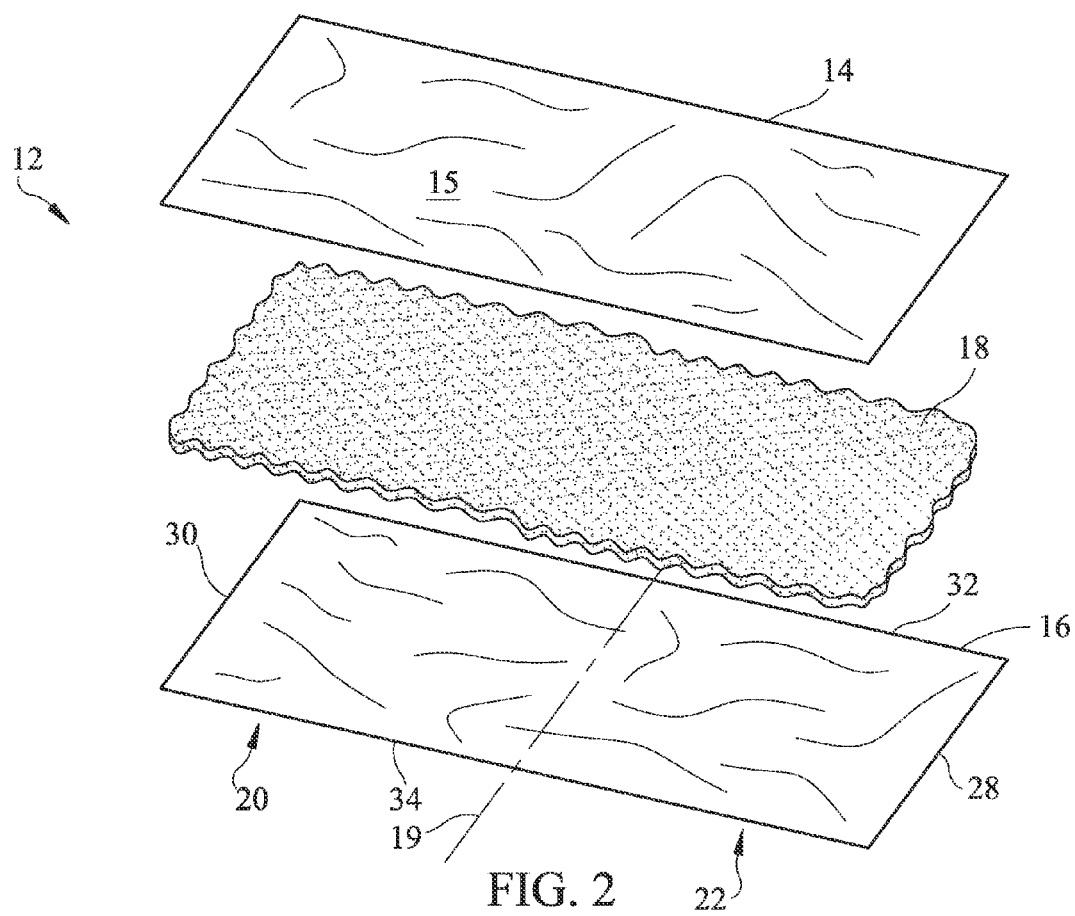
FIG. 2 is an exploded perspective view of the backsheet of FIG. 1, a topsheet, and an absorbent core used in making an absorbent product according to one non-limiting embodiment.
Figure 3:
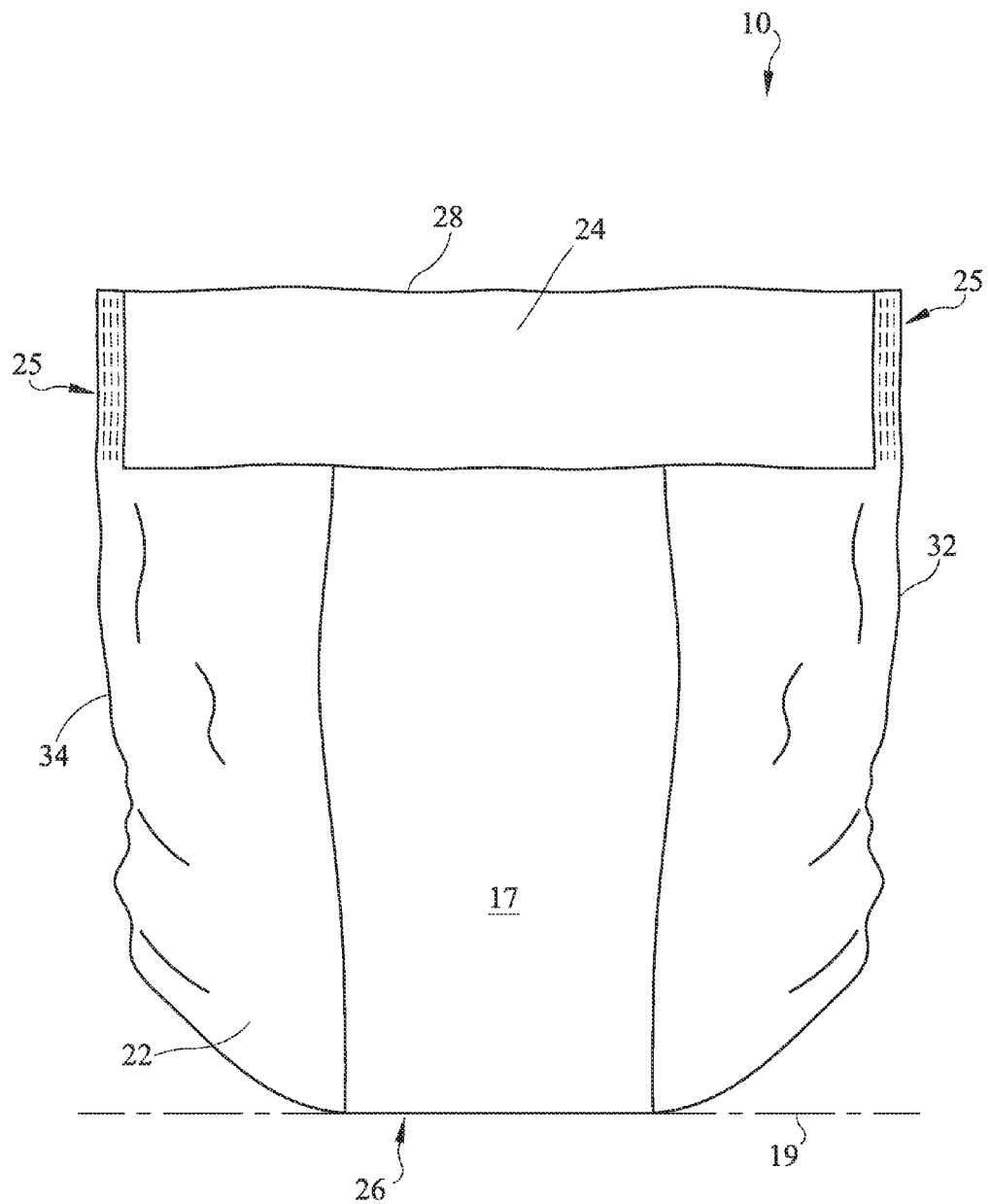
FIG. 3 is a front view of an absorbent product folded about a lateral axis according to one non-limiting embodiment.

In one embodiment, the topsheet 14 of FIG. 2 may be fully or partially elasticized or may be foreshortened to provide a void space between the topsheet 14 and the absorbent core 18. Exemplary structures including elasticized or foreshortened topsheets are described in more detail in U.S. Pat. No. 5,037,416, entitled "Disposable Absorbent Article Having Elastically Extensible Topsheet", issued to Allen et al. on Aug. 6, 1991; and U.S. Pat. No. 5,269,775, entitled "Trisection Topsheets for Disposable Absorbent Articles and Disposable Absorbent Articles Having Such Trisection Topsheets", issued to Freeland et al. on Dec. 14, 1993.

In one embodiment, the absorbent core 18 may comprise any absorbent material that is generally compressible, conformable, non-irritating to the wearer's skin, and capable of absorbing and retaining liquids, such as urine and other certain body exudates, for example. The absorbent core 18 may comprise a wide variety of liquid-absorbent materials commonly used in disposable diapers and other absorbent articles, such as comminuted wood pulp, for example, which is generally referred to as air felt. Examples of other suitable absorbent materials comprise creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. The absorbent core 18 may further comprise minor amounts (typically less than 10%) of non-liquid absorbent materials, such as adhesives, waxes, oils, and the like, for example.

Exemplary absorbent structures for use as the absorbent core 18 are described in U.S. Pat. No. 4,610,678, entitled "High-Density Absorbent Structures", issued to Weisman et al. on Sep. 9, 1986; U.S. Pat. No. 4,834,735, entitled "High Density Absorbent Members Having Lower Density and Lower Basis Weight Acquisition Zones", issued to Alemany et al. on May 30, 1989; U.S. Pat. No. 4,888,231, entitled "Absorbent Core Having A Dusting Layer", issued to Angstadt on Dec. 19, 1989; U.S. Pat. No. 5,260,345, entitled "Absorbent Foam Materials for Aqueous Body Fluids and Absorbent Articles Containing Such Materials", issued to DesMarais et al. on Nov. 9, 1993; and U.S. Pat. No.

5,387,207, entitled "Thin-Unit-Wet Absorbent Foam Materials for Aqueous Body Fluids and Process for Making Same", issued to Dyer et al. on Feb. 7, 1995; and U.S. Pat. No. 5,397,316, entitled "Slitted Absorbent Members for Aqueous Body Fluids Formed of Expandable Absorbent Materials", issued to LaVon et al. on Mar. 14, 1995.

In one embodiment, the backsheet 16 may be joined with the topsheet 14 at least around portions of the outer perimeters of the backsheet 16 and the topsheet 14, thereby sandwiching the absorbent core 18 therebetween. The backsheet 16 can prevent, or at least inhibit, any exudates absorbed by the absorbent core 18 and contained within the absorbent product 10 from soiling other external articles that may contact the absorbent product 10, such as bed sheets, pants, garments, and/or undergarments, for example. In one embodiment, the backsheet 16 may be substantially impervious to liquids (e.g., urine) and may comprise a laminate of a nonwoven and a thin plastic film, such as a thermoplastic film having a thickness of about 0.012 mm to about 0.051 mm, for example. Suitable backsheet films include those manufactured by Tredegar Industries Inc. of Terre Haute, Ind. and sold under the trade names X15306, X10962, and X10964. Other suitable backsheet materials may include breathable materials that permit vapors to escape through the backsheet 16 while still preventing exudates from passing through the backsheet 16. Exemplary breathable materials may include materials such as woven webs, nonwoven webs, composite materials such as film-coated nonwoven webs, and microporous films such as manufactured by Mitsui Toatsu Co., of Japan, under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746, published on Jun. 22, 1995, in the name of E. I. DuPont. Other breathable backsheets including nonwoven webs and apertured formed films are described in U.S. Pat. No. 5,571,096, entitled "Absorbent Article Having Breathable Side Panels", issued to Dobrin et al. on Nov. 5, 1996.

The absorbent product 10 may also comprise other features, such as front and rear ear panels, waist cap features, elastic, and other suitable components, for example, to provide a better fit, better containment, and more pleasant aesthetic characteristics. Various additional features are described in further detail in U.S. Pat. No. 3,860,003, entitled "Contractable Side Portions for Disposable Diaper", issued to Buell on Jan. 14, 1975; and U.S. Pat. No. 5,151,092, entitled "Absorbent Article With Dynamic Elastic Waist Feature Having a Predisposed Resilient Flexural Hinge", issued to Buell et al. on Sep. 29, 1992.

In one embodiment, referring again to FIGS. 1-5, the backsheet 16 can comprise a first lateral end edge 28, a second lateral end edge 30, a first longitudinal side edge 32, and a second longitudinal side edge 34. The first lateral end edge 28 can oppose the second lateral end edge 30 such that when the first portion 20 of the absorbent product 10 is folded about the lateral axis 19 over the second portion 22 of the absorbent product 10, the first lateral end edge 28 can be positioned adjacent to, or substantially adjacent to, the second lateral end edge 30. In one embodiment, the first longitudinal side edge 32 can oppose the second longitudinal side edge 34. When the first portion 20 of the absorbent product 10 is folded over the second portion 22 of the absorbent product 10 about the lateral axis 19, the first longitudinal side edge 32 can be folded over itself such that a first portion of the first longitudinal side edge 32 is positioned adjacent to, or substantially adjacent to, a second portion of the first longitudinal side edge 32. Likewise, the second longitudinal side edge 34 can be folded over itself such that a first portion of the second longitudinal side edge 34 is positioned adjacent to, or substantially adjacent to, a second portion of the second longitudinal side edge 34.

Figure 4:
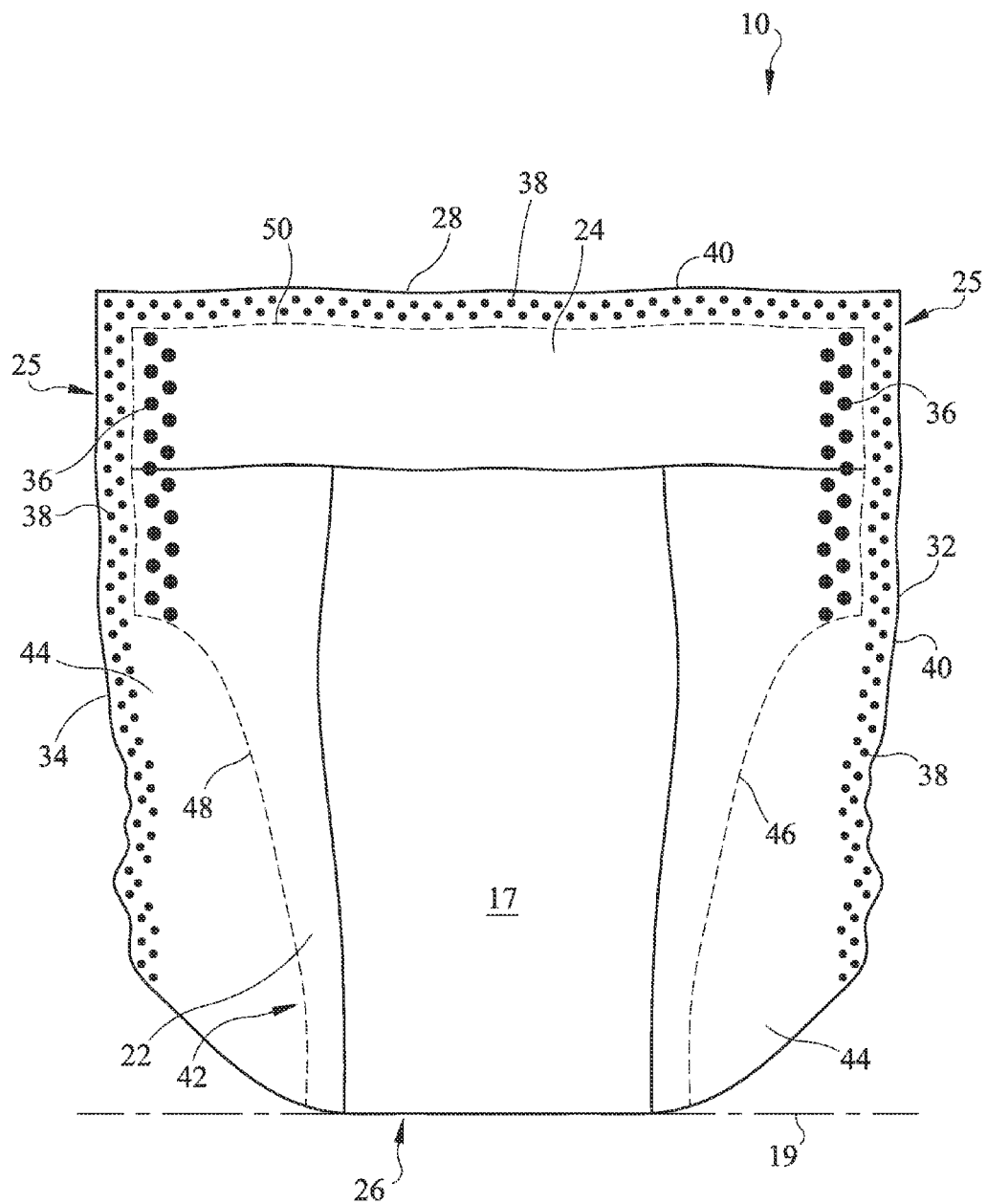
FIG. 4 is a front view of FIG. 3, with various lines of weakness and seals formed in the absorbent product according to one non-limiting embodiment.
Figure 5:
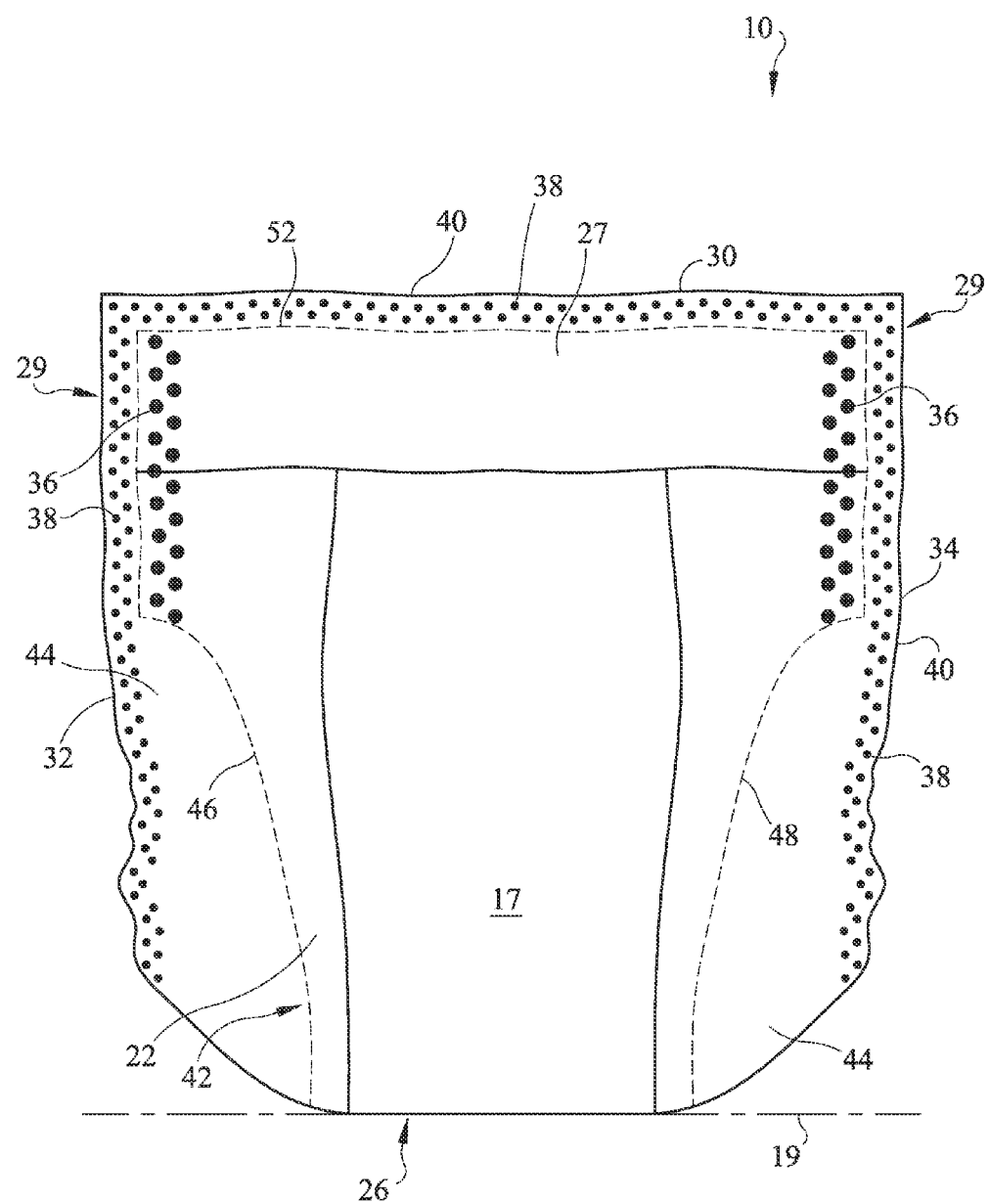
FIG. 5 is a rear view of the absorbent product of FIG. 4 with various lines of weakness and seals formed in the absorbent product according to one non-limiting embodiment.
Figure 6:
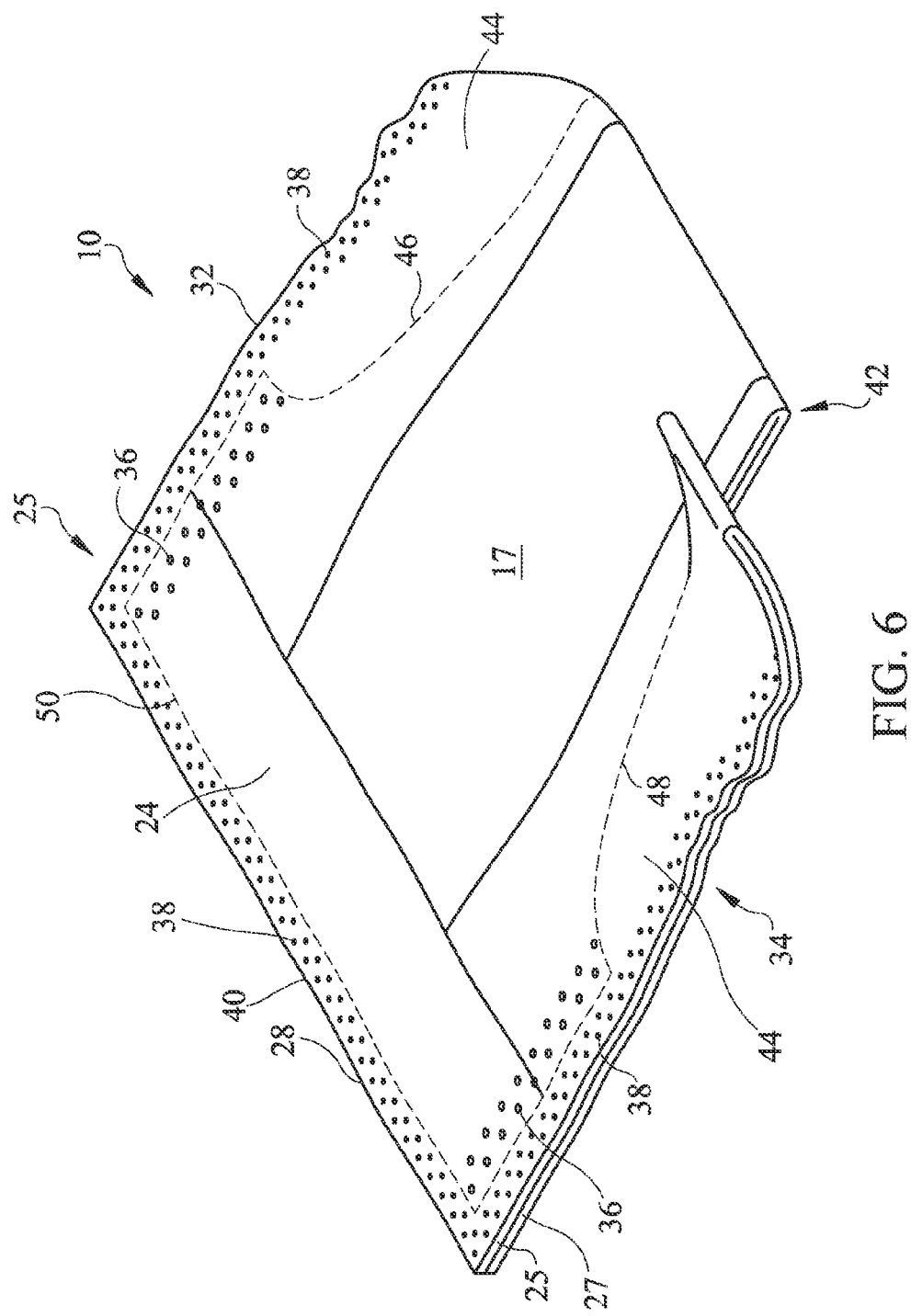
FIG. 6 is a perspective view of FIG. 4 with a removable trim region of the absorbent product partially removed from an absorbent article according to one non-limiting embodiment.

Further to the above, referring to FIGS. 4-6, a seal 38 can be formed partially about an outer perimeter 40, or inboard of the outer perimeter 40, of the absorbent product 10 to seal the first portion 20 to the second portion 22 and help maintain an absorbent article 42 formed within the absorbent product 10 in a sanitary condition prior to being positioned on a wearer. In one embodiment, the seal 38 may not extend through the crotch region 26 of the absorbent product 10, as the crotch region 26 will already be sealed owing to the folding of the first portion 20 over the second portion 22 about the lateral axis 19. The seal 38 can be formed by applying an adhesive near or on the outer perimeter of the first portion 20 and/or the second portion 22 and then applying pressure to the absorbent product 10 to cause the adhesive to seal the first portion 20 to the second portion 22. In other embodiments, the seal 38 can be formed by melting at least a segment of the outer perimeters, or at least a segment proximate to the outer perimeters, of the first and second portions 20 and 22 together using a suitable heating or melting device. It is to be appreciated that other suitable seals and/or methods of sealing are within the scope of the present disclosure. As discussed in further detail below, a separate waist seal 36 can be used to permanently join opposing lateral end portions 25 of the first waist region 24 and opposing lateral end portions 29 of the second waist region 27 to form a waist within the absorbent article 42.

FIG. 4 is a front view of the first portion 20 of the absorbable product 10 and FIG. 5 is a rear view of the second portion 22 of the absorbent product 10. In various embodiments, lines of weakness can be formed in the absorbent product 10 such that a removable trim region 44 can be separated from the absorbent article 42 formed within the absorbent product 10. The removable trim region 44 can comprise the seal 38 thereon. The seal 38 can be defined by having an entire length of the first lateral end edge 28 connected with an entire length of the second lateral end edge 30, an entire length of the first portion of the first longitudinal side edge 32 connected with an entire length of the second portion of the first longitudinal side edge 32, and an entire length of the first portion of the second longitudinal side edge 34 connected with an entire length of the second portion of the second longitudinal side edge 34. In other various embodiments, the seal 38 can be defined by having only segments of the entire length of the first lateral end edge 28 connected with only segments of the entire length of the second lateral end edge 30, only segments of the entire length of the first portion of the first longitudinal side edge 32 connected with only segments of the entire length of the second portion of the first longitudinal side edge 32, and only segments of the entire length of the first portion of the second longitudinal side edge 34 connected with only segments of the entire length of the second portion of the second longitudinal side edge 34. When referring to a connection at an "end edge" or at a "side edge," these terms can also mean proximate to the end edge or proximate to the side edge, respectively. It is to be appreciated that other seal configurations can also be provided and that such seal configurations are within the scope of the present disclosure.

In one embodiment, referring to FIGS. 4-8, the removable trim region 44 can surround the absorbent article 42, with the exception of the crotch region 26, to maintain the absorbent article 42, or the wearer facing surface 15, in a sealed, sanitary condition prior to use by the wearer. The removable trim region 44 can have an area formed between an outer perimeter of the absorbent article 42, the first and second longitudinal side edges 32 and 34, and the first and second lateral end edges 28 and 30. The removable trim region 44 can be configured to be separated from the absorbent article 42 about the lines of weakness formed in the absorbent product 10. After the removable trim region 44 is separated from the absorbent article 42, the removable trim region 44 can be discarded and the absorbent article 42 can be positioned on the wearer. In one embodiment, the removable trim region 44 can comprise a portion of the backsheet 16. In other embodiments, the removable trim region 44 can comprise a portion of the top sheet 14, a portion of the backsheet 16, and/or a portion of the absorbent core 18. In one embodiment, the removable trim region 44 can have lines of weakness defined therein such that it can be readily separated from the absorbent article 42 in portions or sections.

In one embodiment, a first portion of an absorbent article can be folded over a second portion of the absorbent article about a lateral axis of the absorbent article. In such an embodiment, a region of an outer perimeter of the first portion of the absorbent article can be attached to a region of an outer perimeter of the second portion of the absorbent article using an adhesive or a melting technique, for example. Such attachment can help maintain a wearer facing surface of the absorbent article in a sanitary condition prior to use. In one embodiment, the areas of attachment of the region of the outer perimeter of the first portion to the region of the outer perimeter of the second portion can form lines of weakness in the absorbent article. In this embodiment, a user can merely pull the first portion away from the second portion to cause the various lines of weakness to separate prior to use of the absorbent article. The absorbent article can then be placed on a wearer. In such an embodiment, the removable trim region 44 is not required.

In yet another embodiment, certain portions of the absorbent article may be perforated such that upon tearing of the perforation (or line of weakness), the trim remains connected with the absorbent article. For example, only the first waist includes a line of weakness, such that upon removal of trim from the first waist region along the line of weakness, trim along the second waist region would remain connected. In another example, only the side edges on the front or rear side of the absorbent article include lines of weakness, such that upon removal of trim from the front or rear side along the line of weakness, trim on the opposing side would remain connected.

Figure 7:
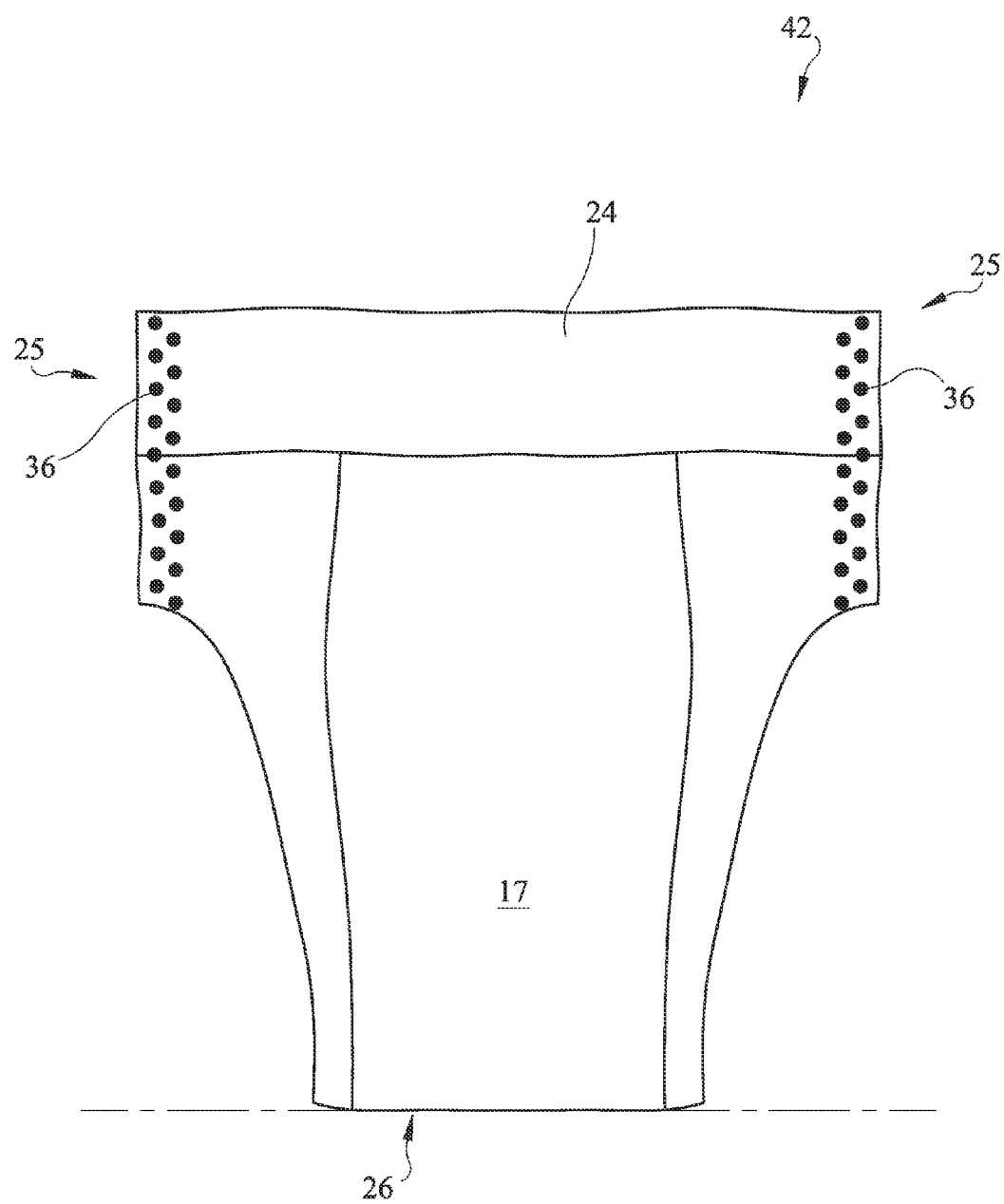
FIG. 7 is a front view of the absorbent product of FIG. 4 with a removable trim region fully removed from an absorbent article, the absorbent article is illustrated in a folded configuration, according to one non-limiting embodiment.
Figure 8:
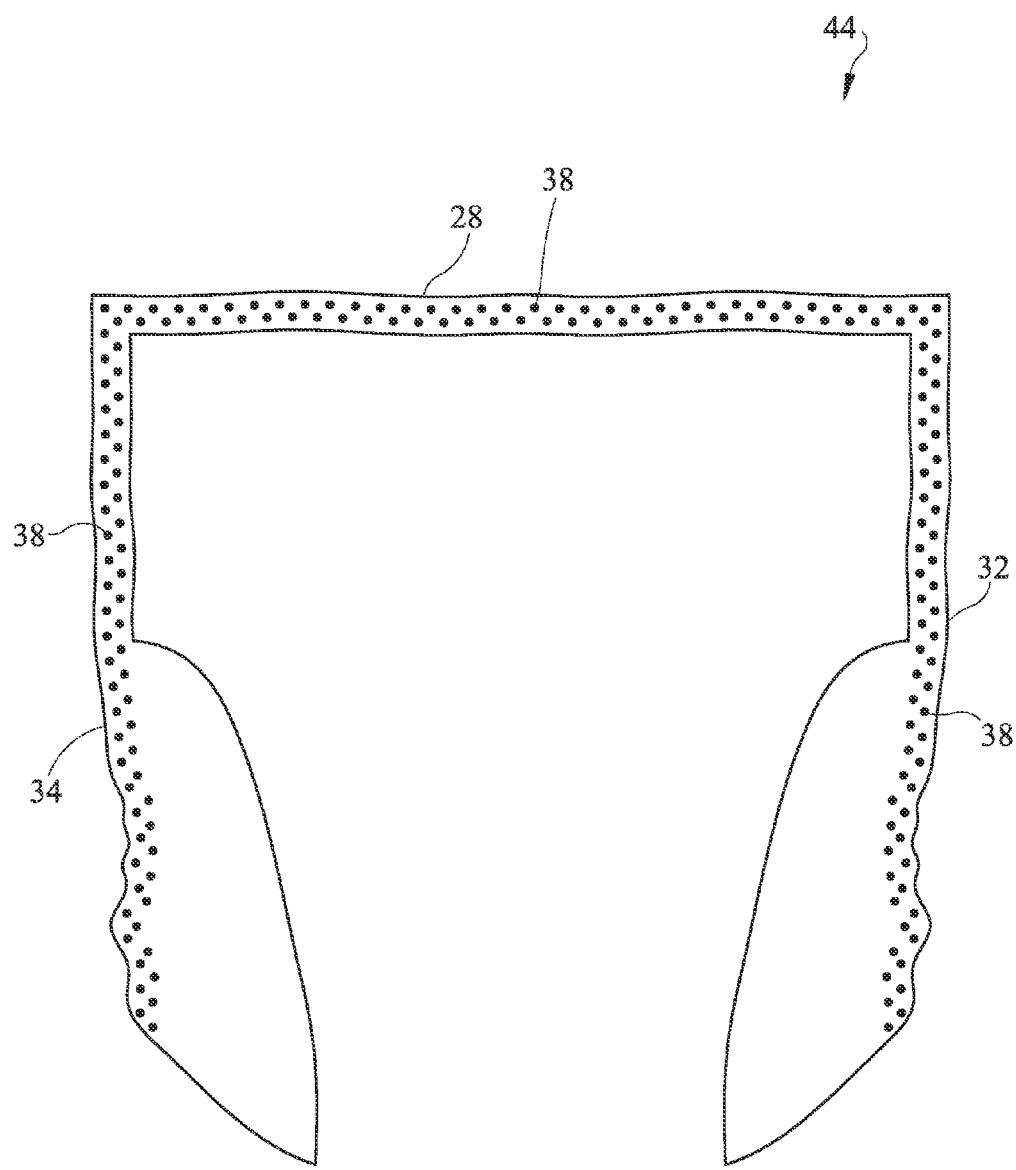
FIG. 8 is a front view of the removable trim region of FIG. 4 fully separated from the absorbent article according to one non-limiting embodiment.

In various embodiments, still referring to FIGS. 4-8, a first longitudinal line of weakness 46 can be formed in the absorbent product 10 laterally inboard of the first longitudinal side edge 32 and a second longitudinal line of weakness 48 can be formed in the absorbent product 10 laterally inboard of the second longitudinal side edge 34. In one embodiment, a first lateral line of weakness 50 can be formed in the absorbent product 10 longitudinally inboard of the first lateral end edge 28 and a second lateral line of weakness 52 (see, FIG. 5) can be formed in the absorbent product 10 longitudinally inboard of the second lateral end edge 30. In various embodiments, the first and second lateral lines of weakness 50 and 52 may be connected to or intersect with the first and second longitudinal lines of weakness 46 and 48. The various lines of weakness can include scored portions in the absorbent product 10, perforated portions in the absorbent product 10, and/or thin or weak portions in the absorbent product 10, for example. In any event, the various lines of weakness can allow the removable trim region 44 to easily be separated from, torn away from, or removed from, the absorbent article 42. The absorbent article 42 with the removable trim region 44 separated therefrom is illustrated in FIG. 7. In one embodiment, referring to FIG. 8, the removable trim region 44 is illustrated after being separated from the absorbent article 42.

Figure 9:
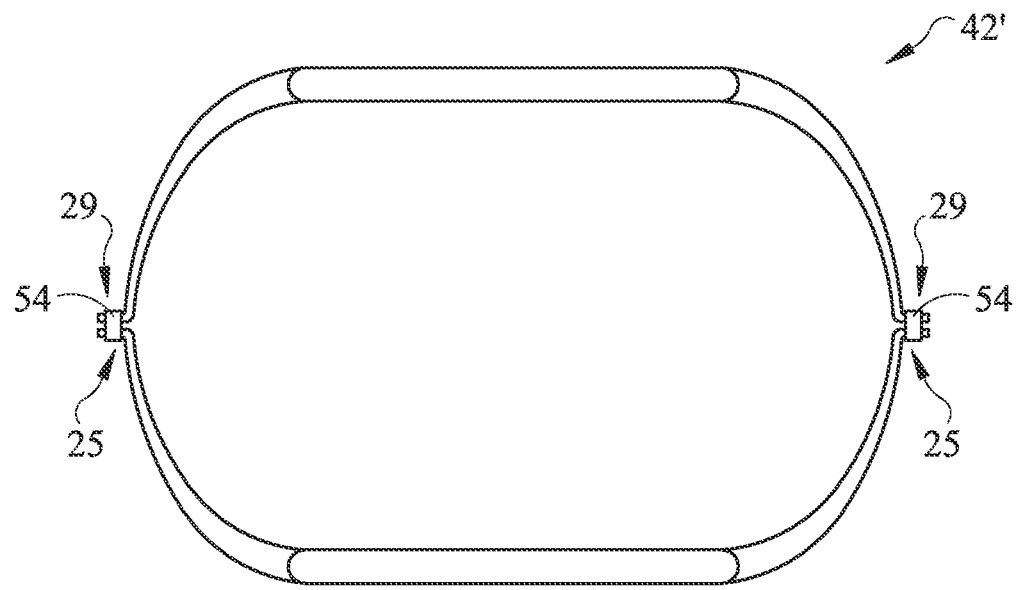
FIG. 9 is a top view of a butt seam formed on an absorbent article according to one non-limiting embodiment.
Figure 10:
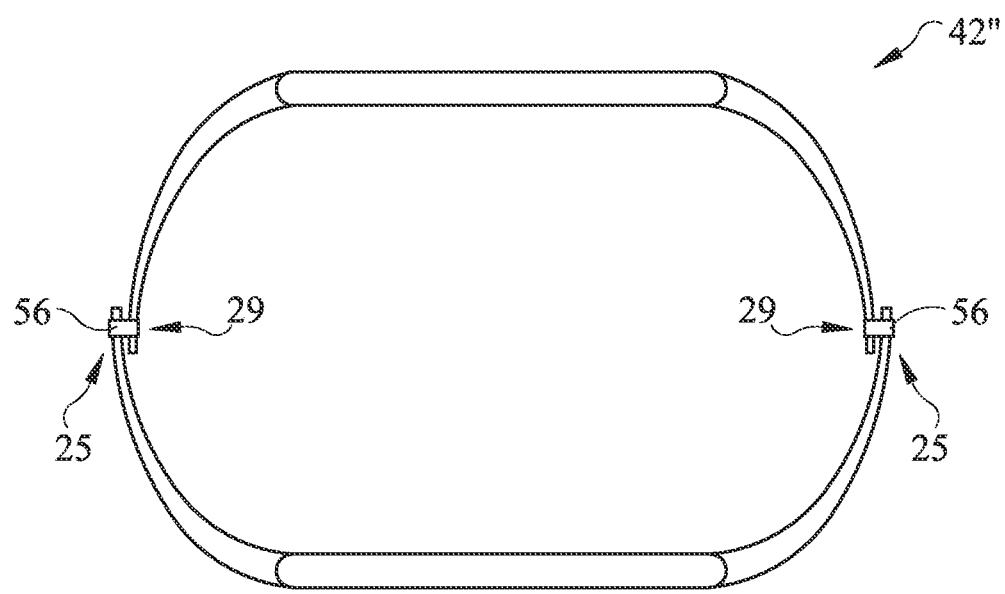
FIG. 10 is a top view of an overlap seam formed on an absorbent article according to one non-limiting embodiment.
Figure 11:
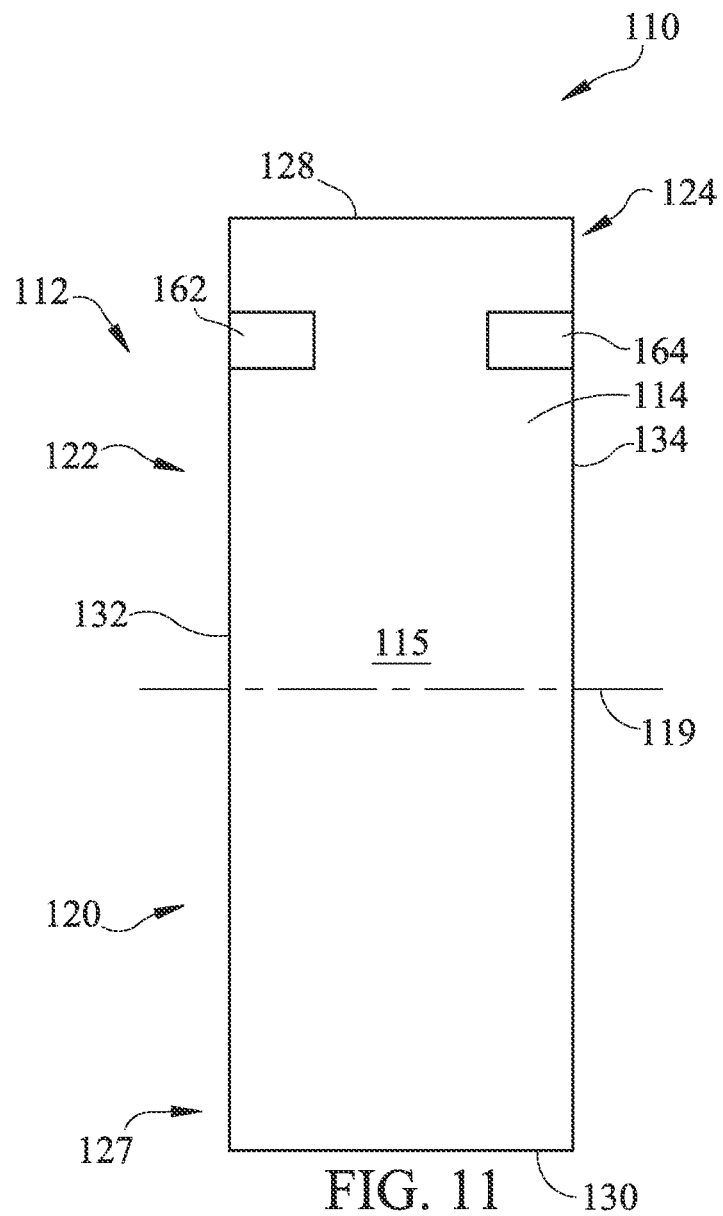
FIG. 11 is a top view of an absorbent product according to one non-limiting embodiment.

In one embodiment, opposing lateral end portions 25 of the first waist region 24 can be permanently connected with opposing lateral end portions 29 of the second waist region 27 to form an absorbent article. In one embodiment, referring to FIG. 9, opposing lateral end portions 25 of the first waist region 24 can be permanently connected to opposing lateral end portions 29 of the second waist region 27 using a butt seam 54 to form absorbent article 42'. In other various embodiments, referring to FIG. 10, the opposing lateral end portions 25 of the first waist region 24 can be permanently connected with the opposing lateral end portions 29 of the second waste region 27 using an overlap seam 56 to form absorbent article 42". In the butt seam embodiment and the overlap seam embodiment, the first and second longitudinal lines of weakness 50 and 52 can define leg openings in the absorbent article 42. More particularly, the first longitudinal line of weakness 50 can define a first leg opening and the second longitudinal line of weakness 52 can define a second leg opening. It is to be appreciated that other suitable seams can also be used with the absorbent article 42 of the present disclosure to attach the opposing lateral end portions 25 of the first waist region 25 to the opposing lateral end portions 29 of the second waist region 27.

In still other various embodiments, in order to keep the absorbent article 42 in place about the wearer, a fastening system (not illustrated) can be used to releasably connect the opposing lateral end portions 25 of the first waist region 24 to the opposing lateral end portions 29 of the second waist region 27 to form leg openings and an absorbent article waist. When fastened, the fastening system carries a tensile load around the absorbent article waist. In one embodiment, the fastening system can be designed to allow a user to hold one element of the fastening system and connect the opposing lateral end portions 25 of the first waist region 24 to the opposing lateral end portions 29 of the second waist region 27. The absorbent articles 42 according to the present disclosure may be provided with a re-closable fastening system or may alternatively be provided in the form of pant-type absorbent articles, such as diapers, for example. The fastening system and any component thereof may include any material suitable for such a use, including but not limited to plastics, films, foams, nonwoven webs, woven webs, paper, laminates, fiber reinforced plastics and the like, or combinations thereof. In one embodiment, the materials that make up the fastening system may be flexible. The flexibility of the materials is designed to allow the fastening system to conform to the shape of the wearer's body and thus, reduce the likelihood that the fastening system will irritate or injure the wearer's skin.

In other various embodiments of the present disclosure, referring to FIGS. 11-14, an absorbent product 110 is provided. In one embodiment, the absorbent product 110 can comprise a chassis 112, similar to chassis 12 described above, which may comprise a main body of the absorbent product 110. The chassis 112 can also comprise an outer covering including a liquid pervious topsheet 114 and/or a liquid impervious backsheet 116. The topsheet 114 can comprise a wearer facing surface 115 and the backsheet 116 can comprise a garment facing surface 117. In one embodiment, the topsheet 114 and the backsheet 116 can be similar to the topsheet 14 and the backsheet 16 discussed above. An absorbent core (not illustrated) can be formed or positioned in the chassis 112 intermediate the topsheet 114 and the backsheet 116, similar to the absorbent core 18 discussed above. In one embodiment, the chassis 112 can be folded about a lateral axis 119 such that a first portion 120 of the chassis 112 can be positioned adjacent to, or substantially adjacent to, (i.e., folded over) a second portion 122 of the chassis 112. In such an embodiment, the first and second portions 120 and 122 of the chassis 112 can form a first waist region 124, a second waist region 127, and a crotch region 126 longitudinally intermediate of the first and second waist regions 124 and 127. In one embodiment, the first and second waist regions 124 and 127 may comprise elastic elements such that they gather about the waist of the wearer to provide improved fit and containment. The crotch region 126 is the portion of the absorbent product 110 which is generally positioned between the wearer's legs.

In addition to the above discussed features, referring to FIGS. 12-16, the first waist region 124 can comprise first and second ears 158 and 158', wherein each ear can extend outwardly from an absorbent article 142, and the second waist region 127 can comprise third and fourth ears 160 and 160', wherein each ear can extend outwardly from the absorbent article 142. The first waist region 124 can comprise opposing lateral ends 125 and the second waist region 127 can comprise opposing lateral ends 129. In one embodiment, a first fastener 162 can be positioned on or attached to the first ear 158 and a second fastener 164 can be positioned on the second ear 158'. Of course, the third and fourth ears 160 and 160' can also comprise first and second fasteners, for example. In one embodiment, the third ear 160 and the fourth ear 160' can each comprise a material configured to be attached to a portion of the first and second fasteners 162 and 164. In one embodiment, the first and second fasteners 162 and 164 can comprise a material comprising a plurality of loops, while the material of the third and fourth ears 160 and 160' can comprise a plurality of hooks, for example. In other embodiments, the first and second fasteners 162 and 164 can comprise an adhesive configured to be attached to portions of the third and fourth ears 160 and 160'.

In one embodiment, referring to FIGS. 11-14, the absorbent product 110, the topsheet 114, and/or the backsheet 116 can comprise a first lateral end edge 128 and a second lateral end edge 130. The first lateral end edge 128 can oppose the second lateral end edge 130 when the first portion 120 of the absorbent product 110 is not folded over the second portion 122 of the absorbent product 110 about the lateral axis 119 and the first lateral end edge 128 can be positioned adjacent to, or substantially adjacent to, the second lateral end edge 130 when the first and second portions 120 and 122 of the absorbent product 110 are folded about the lateral axis 119. In one embodiment, the absorbent product 110 can also comprise a first longitudinal side edge 132 that can oppose a second longitudinal side edge 134 when the absorbent portion 110 is not folded about the lateral axis 119. When the first portion 120 of the absorbent product 110 is folded over the second portion 122 of the absorbent product 110 about the lateral axis 119, the first longitudinal side edge 132 can be folded over itself such that a first portion of the first longitudinal side edge 132 can be positioned adjacent to, or substantially adjacent to, a second portion of the first longitudinal side edge 132. Likewise, the second longitudinal side edge 134 can be folded over itself such that a first portion of the second longitudinal side edge 134 can be positioned adjacent to, or substantially adjacent to, a second portion of the second longitudinal side edge 134.

Figure 12:
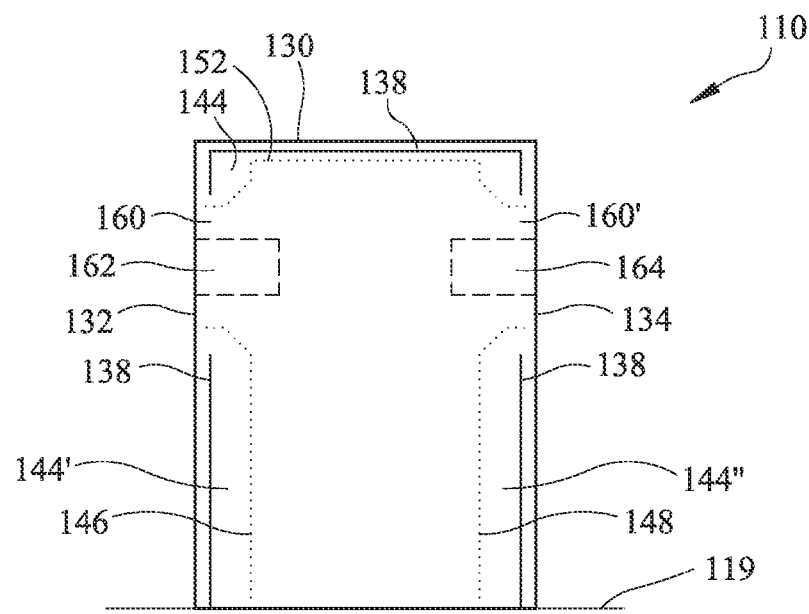
FIG. 12 is a front view of the absorbent product of FIG. 11 folded about a lateral axis according to one non-limiting embodiment.
Figure 13:
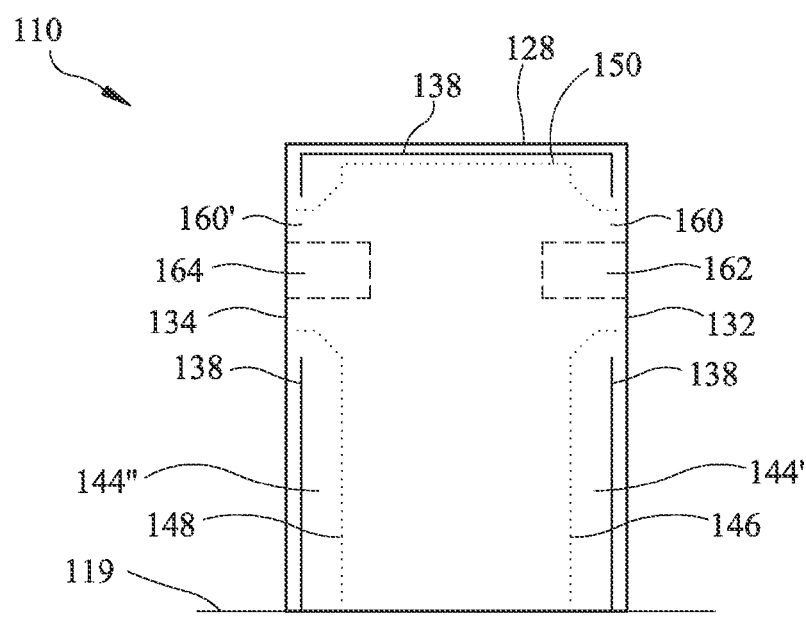
FIG. 13 is a rear view of the absorbent product of FIG. 11 folded about a lateral axis according to one non-limiting embodiment.
Figure 14:
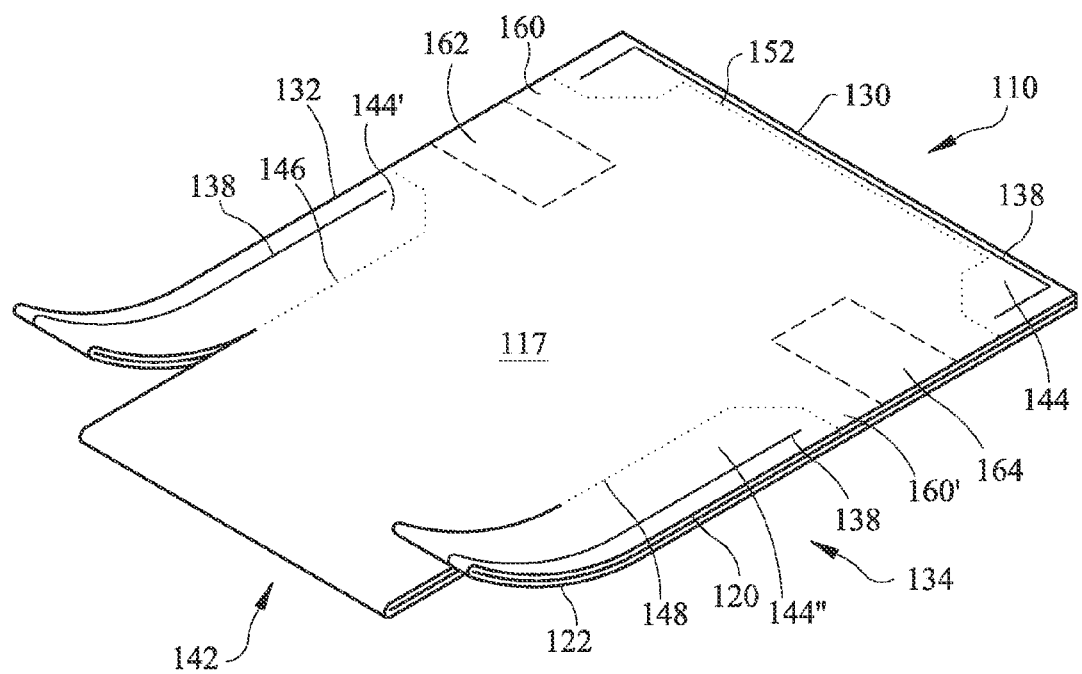
FIG. 14 is a perspective view of FIGS. 12 and 13 with removable trim regions partially separated from an absorbent article formed in the absorbent product according to one non-limiting embodiment.

In various embodiments, referring to FIGS. 12-14, a first longitudinal line of weakness 146 can be formed in the absorbent product 110 laterally inboard of the first longitudinal side edge 132 and a second longitudinal line of weakness 148 can be formed in the absorbent product 110 laterally inboard of the second longitudinal side edge 134. In one embodiment, a first lateral line of weakness 150 can be formed in the absorbent product 110 longitudinally inboard of the first lateral end edge 128 (see, FIG. 13) and a second lateral line of weakness 152 can be formed in the absorbent product 110 longitudinally inboard of the second lateral end edge 130. In various embodiments, although not illustrated, the first and second lateral lines of weakness 150 and 152 may be connected to or may intersect with the first and second longitudinal lines of weakness 146 and 148. In other embodiments, the first lateral line of weakness 150 can terminate proximate to the first ear 158 on a first end and can terminate proximate to the second ear 158' on a second end. Similarly, the second lateral line of weakness 152 can terminate proximate to the third ear 160 on a first end and can terminate proximate to the fourth ear 160' on a second end. In one embodiment, the first longitudinal line of weakness 146 can terminate proximate to the first ear 158 at a first end and can terminate proximate to the third ear 160 at a second end. Likewise, the second longitudinal line of weakness 148 can terminate proximate to the second ear 158' at a first end and can terminate proximate to the fourth ear 160' at a second end.

As a result of the above, three removable trim regions can be formed in the absorbent product 110 when the absorbent product 110 is folded about the lateral axis 119. In one embodiment, referring to FIGS. 12-14 and 17, a first removable trim region 144 can be formed intermediate the first and second lateral lines of weakness 150 and 152 and the first and second lateral end edges 128 and 130. A second removable trim region 144' can be formed intermediate the first longitudinal line of weakness 146 and the first longitudinal side edge 132. A third removable trim region 144" can be formed intermediate the second longitudinal line of weakness 148 and the second longitudinal side edge 134. Similar to the removable trim region 44 discussed above, each of the first, second, and third removable trim regions 144, 144', and 144" can each comprise a seal 138. The seal 138 can be similar to the seal 38 discussed above. In one embodiment, the seal 138 can extend along an entire length of each of the removable trim regions 144, 144', and 144". In other embodiments, the seal 138 can extend along a portion of the entire length of the removable trim regions 144, 144', and 144". In such an embodiment, owing to the seal 138, the removable trim regions 144, 144', and 144" can maintain the wearer facing surface 115 of the absorbent article 142 in a sanitary condition while the removable trim regions 144, 144', and 144" are attached to the absorbent article 142.

Figure 15:
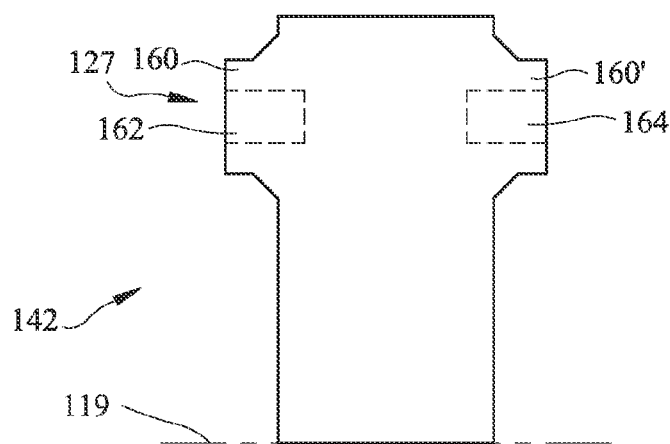
FIG. 15 is a front view of the absorbent article formed from the absorbent product of FIGS. 12 and 13 after the removable trim regions are fully separated from an absorbent article, with the absorbent article is in a folded configuration, according to one non-limiting embodiment.
Figure 16:
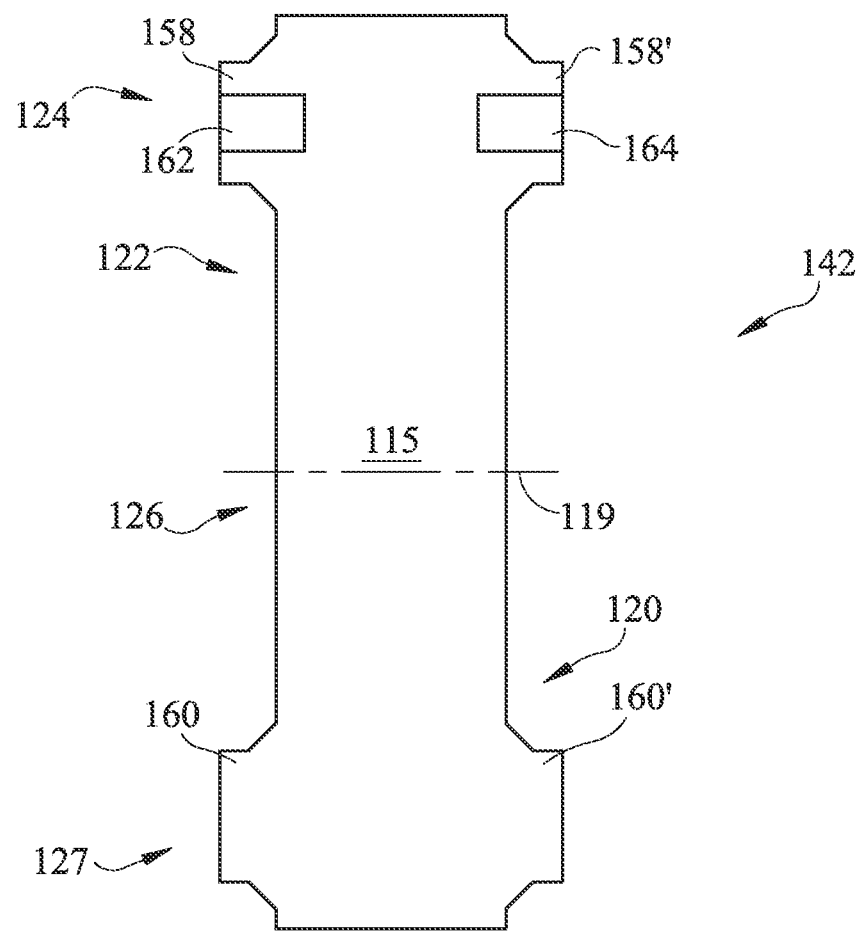
FIG. 16 is a top view of the absorbent article of FIG. 15 in an unfolded configuration according to one non-limiting embodiment.
Figure 17:
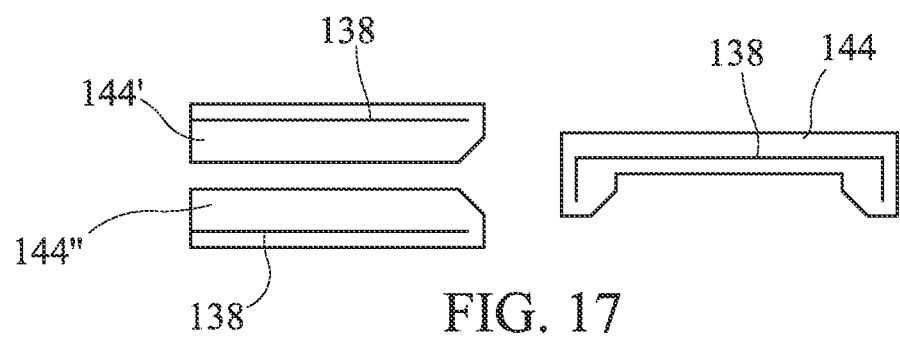
FIG. 17 is a top view of the removable trim regions of FIG. 14 after they have been fully separated from the absorbent article according to one non-limiting embodiment.

The various lines of weakness 146, 148, 150, and 152 can comprise scored portions in the absorbent product 110, perforated portions in the absorbent product 110, and/or thin or weak portions in the absorbent product 110, for example. In any event, referring to FIG. 14, prior to use of the absorbent article 142, the removable trim regions 144, 144', and 144" can be separated from, removed from, and/or torn away from the absorbent article 142 about the various lines of weakness and discarded. The absorbent article 142 can then be positioned on a wearer. In one embodiment, the absorbent article 142 is illustrated in FIG. 15 in a folded configuration with the removable trim regions 144, 144', and 144" separated therefrom. In one embodiment, referring to FIG. 16, the absorbent article 142 is illustrated in an unfolded configuration. In one embodiment, referring to FIG. 17, the removable trim regions 144, 144', and 144" are illustrated after being removed from the absorbent product 142.

In one embodiment, a method for manufacturing an absorbent product can comprise the steps of advancing a continuous substrate through a converting line and combining the substrate with a topsheet and an absorbent core. In such an embodiment, the absorbent core can be disposed between the topsheet and the substrate. In one embodiment, the substrate can then be cut to form a backsheet having a first lateral end edge, a second lateral end edge, a first longitudinal side edge, and a second longitudinal side edge. The backsheet and/or the backsheet, the absorbent core, and the topsheet can then be folded about a lateral axis to position the first lateral end edge adjacent to, or substantially adjacent to, the second lateral end edge, to position a first portion of the first longitudinal side edge adjacent to, or substantially adjacent to, or substantially adjacent to, a second portion of the first longitudinal side edge, and to position a first portion of the second longitudinal side edge adjacent to, or substantially adjacent to, a second portion of the second longitudinal side edge. After such positioning, the first lateral end edge can be connected to the second lateral end edge, the first portion of the first longitudinal side edge can be connected to the second portion of the first longitudinal side edge, and the first portion of the second longitudinal side edge can be connected to the second portion of the second longitudinal side edge. The connection between the various portions can comprise a seal, such as a heat seal or an adhesive seal, for example. A first longitudinal line of weakness can then be created laterally inboard of the first longitudinal end edge, a second longitudinal line of weakness can be created laterally inboard of the second longitudinal end edge, a first lateral line of weakness can be created longitudinally inboard of the first lateral end edge, and a second lateral line of weakness can be created longitudinally inboard of the second lateral end edge. In one embodiment, the various lines of weakness can define an outer perimeter of an absorbent article comprising an absorbent core disposed between the backsheet and the topsheet. A removable trim region can be defined by an area of the backsheet between the outer perimeter of the absorbent article and the first and second longitudinal side edges and the first and second lateral end edges.

Further to the above, in one embodiment, the absorbent article can comprise a diaper having a wearer facing surface defined by the topsheet and a garment facing surface defined by the backsheet. The absorbent article can have longitudinally opposing first and second waist regions adjacent to, or substantially adjacent to, the first and second lateral lines of weakness and a crotch region longitudinally intermediate of the first and second waist regions. Opposing lateral end portions of the first waist region can be connected with opposing lateral end portions of the second waist region to form a waist opening. In one embodiment, the connection between the first and second waist regions can comprise overlap seams or butt seams, for example. In one embodiment, the first and second longitudinal lines of weakness can define leg openings in the absorbent article. In an embodiment where the absorbent article comprises ears, first and second ears can be connected to the first waist region. The first and second ears can be configured to releasably connect to the second waist region, or ears formed thereon, to form a waist opening in the absorbent article.

In one embodiment, the various lines of weakness can be formed in the backsheet or in the backsheet, the topsheet, and/or the absorbent core by perforating the backsheet or by perforating the backsheet, the topsheet, and/or the absorbent core using a perforating device or a cutting member, for example. In other embodiments, the various lines of weakness can be formed in the backsheet or formed in the backsheet, the topsheet, and/or the absorbent core by scoring the backsheet or by scoring the backsheet, the topsheet, and/or the absorbent core using a scoring device, for example. In one embodiment, the first and second lateral lines of weakness can be connected to or can intersect with the first and second longitudinal lines of weakness.

In one embodiment, the first portion of the absorbent product and the second portion of the absorbent product can be sealed to each other within the area of the removable trim region or, in other embodiments, within the areas of the removable trim regions. In one example embodiment, an entire length of the first lateral end edge can be sealed with an entire length of the second lateral end edge; an entire length of the first portion can be sealed with an entire length of the second portion of the first longitudinal side edge; and an entire length of the first portion can be sealed with an entire length of the second portion of the second longitudinal side edge. In other embodiments, the seal can be intermittent along various portions of the removable trim regions, for example. In such an embodiment, the intermittent seal can join the first portion of the absorbent product with the second portion of the absorbent product such that a wearer facing surface of the absorbent article can remain in a sanitary condition prior to use of the absorbent article.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:
1. A method for manufacturing an absorbent product comprising the steps of:
   advancing a continuous substrate through a converting line;

combining the substrate with a topsheet and an absorbent core, wherein the absorbent core is disposed between the topsheet and the substrate;

cutting the substrate to form a backsheet having a first lateral end edge, a second lateral end edge, a first longitudinal side edge, and a second longitudinal side edge;

folding the backsheet along a lateral axis;

connecting the first lateral end edge with the second lateral end edge, a first portion of the first longitudinal side edge with a second portion of the first longitudinal side edge, and a first portion of the second longitudinal side edge with a second portion of the second longitudinal side edge; and creating a first longitudinal line of weakness laterally inboard of the first longitudinal end edge, a second longitudinal line of weakness laterally inboard of the second longitudinal end edge, a first lateral line of weakness longitudinally inboard of the first lateral end edge, and a second lateral line of weakness longitudinally inboard of the second lateral end edge, wherein the lines of weakness define an outer perimeter of an absorbent article comprising the absorbent core disposed between the backsheet and the topsheet, and wherein a removable trim region is defined by an area of the backsheet between the outer perimeter of the absorbent article and the first and second longitudinal side edges and the first and second lateral end edges.

2. The method of claim 1, wherein the absorbent article comprises a diaper having a wearer facing surface defined by the topsheet and a garment facing surface defined by the backsheet, and having longitudinally opposing first and second waist regions adjacent to the first and second lateral lines of weakness, and a crotch region longitudinally intermediate of the waist regions.

3. The method of claim 2, further comprising the step of connecting the first waist region with the second waist region to form a waist opening.

4. The method of claim 3, wherein the connections between the first and second waist regions comprise overlap seams.

5. The method of claim 3, wherein the connections between the first and second waist regions comprise butt seams.

6. The method of claim 2, wherein the first and second longitudinal lines of weakness define leg openings.

7. The method of claim 2, further comprising the step of connecting first and second ears with the first waist region, wherein the first and second ears are configured to releasably connect with the second waist region to form a waist opening.

8. The method of claim 1, wherein the first and second lateral lines of weakness are connected with the first and second longitudinal lines of weakness.

9. The method of claim 1, wherein the step of creating lines of weakness comprising perforating the backsheet.

10. The method of claim 1, further comprising the step of sealing: an entire length of the first lateral end edge and an entire length of the second lateral end edge; an entire length of the first portion with an entire length of the second portion of the first longitudinal side edge; and an entire length of the first portion with an entire length of the second portion of the second longitudinal side edge.

* * * * *